United States Patent [19]

Schmitt

[11] Patent Number: 4,609,708

[45] Date of Patent: Sep. 2, 1986

[54] METHOD FOR MANUFACTURE OF POLYMERIC PYRROLIDINIUM METHANESULFONATE VISCOSIFIERS

[75] Inventor: Kirk D. Schmitt, Pennington, N.J.

[73] Assignee: Mobil Oil Corporation, New York, N.Y.

[21] Appl. No.: 695,508

[22] Filed: Jan. 28, 1985

Related U.S. Application Data

[60] Division of Ser. No. 413,574, Aug. 31, 1982, Pat. No. 4,504,622, which is a continuation-in-part of Ser. No. 373,553, Apr. 30, 1982, Pat. No. 4,528,383.

[51] Int. Cl.$^4$ ................................................ C08F 8/34

[52] U.S. Cl. .................................... 525/61; 525/328.2; 525/344

[58] Field of Search ..................... 525/61, 328.2, 328.3

Primary Examiner—Christopher A. Henderson
Attorney, Agent, or Firm—Alexander J. McKillop; Michael G. Gilman; Stanislaus Aksman

[57] ABSTRACT

There are provided polymeric pyrrolidinium methanesulfonate viscosifiers which are useful in chemical waterflooding and in drilling fluids. These compounds may be formed by an unexpected cyclization reaction of quaternary diallyl amino groups on polymeric backbones involving the reaction of such groups with bisulfite salts.

8 Claims, No Drawings

METHOD FOR MANUFACTURE OF POLYMERIC PYRROLIDINIUM METHANESULFONATE VISCOSIFIERS

CROSS-REFERENCE TO RELATED APPLICATIONS

This application is a divisional of a pending U.S. patent application Ser. No. 413,574, filed on Aug. 31, 1982, now U.S. Pat. No. 4,504,622 which was a continuation-in-part of a U.S. patent application Ser. No. 373,553, filed Apr. 30, 1982, now U.S. Pat. No. 4,528,383.

This application is further related to U.S. application Ser. No. 391,214, filed June 23, 1982, in the name of Kirk D. Schmitt, now U.S. Pat. No. 4,458,048, which relates to alkyl sulfonate salts derived from polyvinyl alcohols which are viscosifiers, e.g., for use in enhanced oil recovery fluids and for use in drilling fluids.

The entire disclosure of all of the above-identified patent applications and patents are incorporated herein by reference.

BACKGROUND

The present invention relates to polymeric pyrrolidinium methane sulfonates which are viscosifiers, e.g., for use in enhanced oil recovery fluids and for use in drilling fluids. The invention further relates to methods for making sulfonates.

In the recovery of oil from oil-bearing reservoirs, it usually is possible to recover only minor portions of the original oil in place by the so-called primary recovery methods which utilize only the natural forces present in the reservoir. Thus a variety of supplemental recovery techniques have been employed in order to increase the recovery of oil from subterranean reservoirs. The most widely used supplemental recovery technique is waterflooding which involves the injection of water into an oil-bearing reservoir. As the water moves through the reservoir, it acts to displace oil therein to a production system composed on one or more wells through which the oil is recovered.

One difficulty often encountered in waterflooding operations is the relatively poor sweep efficiency of the aqueous displacing medium; that is, the injected displacing medium tends to channel through certain portions of the reservoir as it travels from the injection system to the production system and to bypass other portions. Such poor sweep efficiency or macroscopic displacement efficiency may be due to a number of factors such as differences in the mobilities of the injected displacing liquids and the displaced reservoir oil and permeability variations within the reservoir which encourage preferential flow through some portions of the reservoir at the expense of other portions.

Various techniques have been proposed in order to improve the sweep efficiency of the injected displacing medium and thus avoid premature breakthrough at one or more of the wells comprising the production system. The most widely used procedure involves the addition of thickening agents to the injected displacing medium in order to increase the viscosity thereof and thus decrease its mobility to a value equal to or less than the mobility of the displaced reservoir oil, resulting in a "mobility ratio" of oil to water which is less than or equal to one. Many polymeric thickening agents including both anionic and cationic polyelectrolytes have been proposed for use in such mobility control operations. Thus, U.S. Pat. No. 3,085,063 discloses waterflooding in which the water is thickened by the addition of polyvinyl aromatic sulfonates such as sulfonated polystyrene and copolymers of such vinyl aromatic sulfonates. Similarly, U.S. Pat. No. 3,984,333 discloses waterflooding involving the injection of an aqueous solution thickened by block copolymers in which the water-soluble blocks are sulfonated polyvinylarenes and the relatively water-insoluble blocks are polymerized alpha olefins and/or hydrogenated dienes such as polyisoprene and polybutadiene. Synthetic anionic polymers such as those disclosed in the patents discussed above, as well as the more widely used partially hydrolyzed polyacrylamides, suffer a number of disadvantages in actual operations. Where the injected water or the reservoir water contains significant quantities of dissolved inorganic salts, their viscosity yield is decreased materially. Also U.S. Pat. No. 3,969,592 discloses water-soluble polymers manufactured by treating an aqueous suspension of protein with selected enzymes.

Also U.S. Pat. No. 4,110,232 discloses a waterflooding process for producing oil wherein an aqueous solution of a copolymer formed of hydrophobic olefinic segments and cationic aromatic segments is injected into oil-containing subterranean formation, and U.S. Pat. No. 4,222,881 discloses a waterflood oil recovery process involving the use of an amphoteric polyelectrolyte as a thickening agent for mobility control comprising a copolymer of a quaternary vinyl pyridinium sulfonate-styrene block copolymers.

During the drilling of an oil well, a usually aqueous fluid is injected into the well through the drill pipe and recirculated to the surface in the annular area between the well-bore wall and the drill string. The functions of the drilling fluid include: lubrication of the drill bit, transportation of cuttings to the surface, overbalancing formation pressure to prevent an influx of oil, gas or water into the well, maintenance of hole stability until casings can be set, suspension of solids when the fluid is not being circulated, and minimizing fluid loss into and possible associated damage/instability to the formation through which drilling is taking place.

Proper overbalancing of formation pressure is obtained by establishing fluid density at the desired level usually via the addition of barite (greater than or equal to 95% barium sulfate). Transportation of cuttings and their suspension when the fluid is not circulating is related to the fluid viscosity and thixotropy which depend on solids content and/or use of a polymer. Filter loss control is obtained also by the use of clays and/or added polymers.

Fluid properties are constantly monitored during the drilling operations and tailored to accommodate the nature of the formation stratum being encountered at the time. When drilling reaches the producing formation special concern is exercised. Preferentially low solids content fluids are used to minimize possible productivity loss by solids plugging. Proper fluid density for overbalancing formation pressure may be obtained by using high salt concentration aqueous brines while viscosity and filter loss control may be obtained by polymer addition. Substantial future oil well drilling will be at depths between 15 and 30 thousand feet where temperatures encountered can be 350° F. Temperatures such as these, coupled with the desire for low solids content and preferably no added solids, require brine tolerant and high temperature stable polymers for viscosity and filtration control. Conventionally employed polymers such as starch, carboxymethyl cellulose, and modified polyacrylates are not stable at the temperatures in question and some have severe brine tolerance limitations.

SUMMARY OF THE INVENTION

According to an aspect of the invention, there is provided a polymeric pyrrolidinium methane sulfonate salt. More particularly, this polymeric pyrrolidinium methane sulfonate salt may be a polymeric backbone having side chain groups of the formula

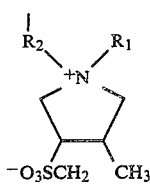

(I)

where:
 (i) $R_1$ is $CH_3$, $CH_2CH_3$, $CH_2CH_2OH$, propyl, butyl or phenyl;
 (ii) $R_2$ is $(CH_2)_n$ or

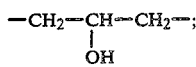

and
 (iii) n is 1–5.
Such a polymeric sulfonate may have the formula

H—$R_3$—H   (II)

wherein $R_3$ represents repeating polymeric units, said units comprising
 (i) units of the formula

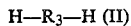  (III)

and (ii) units of the formula

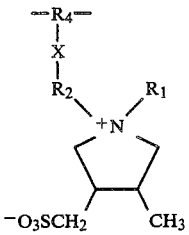  (IV)

where:
 (a) $R_4$ of formulae III and IV are the same organic moiety; and
 (b) X is —NH— or —O—.

The polymeric backbone may be a grafted polymeric backbone, e.g., selected from the group consisting of grafted polyvinyl amines, grafted polyvinyl alcohols and grafted carbohydrate derived polymers.

DETAILED DESCRIPTION

The incorporation of from about 5 to 70 mer % of side groups of formula I onto the alcohol oxygens of polyvinyl alcohols imparts solubility to resulting polymers at high concentrations of salt and divalent ions.

As with all anionic polymers, the viscosity of aqueous solutions of these polymers falls with increasing salt content but, unlike most other anionic polymers, at a salt concentration equivalent to about 10% w/v NaCl the viscosity begins to increase so that by about 20–25% salt the viscosity is as high or higher than in deionized water. The effect of rising salt concentration is independent of the cation used which makes these polymers eminently suitable for enhanced oil recovery in reservoirs of higher brine content or for use in drilling fluids where high concentrations of calcium or other divalent ions may be present. The polymers are extremely stable both thermally and hydrolytically which also lends to their utility in the above-named processes.

The sulfonates according to the present invention may be prepared by a particular combination of process steps many of which may be carried out according to conventional technology. For example, such a sulfonate may be prepared according to the following reaction sequence:

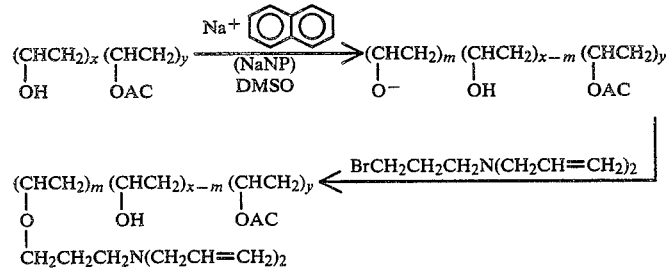

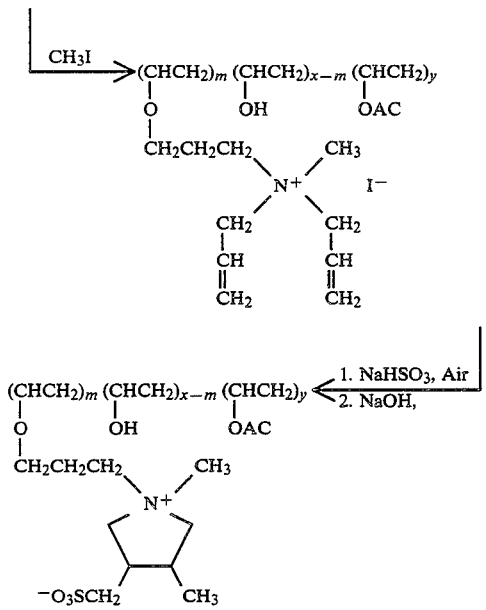

In the above sequence, it is expressly noted that no stereochemical regularity is implied by the structures given. It is also noted that the number calculated by the formula, $(m/x+y) \times 100$, corresponds to the value for mer %.

Since polyvinyl alcohol is customarily made from the hydrolysis of polyvinyl acetate, it is likely that the polymeric alkyl sulfonate salt of formula (I) may contain units of the formula

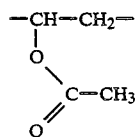

The polymeric sulfonates derived from polyvinyl alcohol may have a molecular weight of at least 25,000, e.g., from about 30,000 to about 500,000. It is contemplated that the higher molecular weight compounds made from super-high viscosity polyvinyl alcohols will have the most desirable thickening properties for mobility control fluids and drilling fluids.

In view of the compatibility of compositions used in the present invention with divalent metal ions, a preferred application of the invention is in reservoirs in which the connate water contains significant divalent ion concentrations and in situations where the available water for flooding or drilling contains divalent metal ions inconsistent with the use of conventional non-brine tolerant thickeners. Thus, a preferred application of the present invention is in those situations in which the reservoir waters and/or the waters employed in formulating the flooding medium or drilling fluid exhibit a divalent metal ion concentration of at least 0.1 weight percent. The invention is particularly useful where the reservoir, injection, and/or drilling waters have divalent metal ion concentrations of 0.5 weight percent or more. A similar consideration applies with regard to those situations in which the waters exhibit moderate to relatively high salinities even though the divalent metal ion concentration may be relatively low. Thus, another application of the invention in those situations in which the reservoir, injection and/or drilling waters have salinities of at least 5.0 weight percent, especially at least 10 weight percent, whether provided by monovalent salts such as sodium chloride or monovalent salts and divalent salts such as calcium or magnesium chloride.

The amount of polymeric pyrrolidinium methane sulfonate salt which may be used in accordance with aspects of the invention should be sufficient to achieve the desired thickening effect. For example, this compound may be added to water and injected into an oil-containing formation in a sufficient amount and concentration to effectively thicken the water so as to provide improved efficiency in driving the oil through the formation to the production well. This thickening agent may be added in concentrations so as to provide a graded viscosity at the trailing edge of the mobility control slug as disclosed in a paper by W.R. Foster entitled "A Low-Tension Waterflooding Process", Journal of Petroleum Technology, Vol. 25, Feb. 1973, pp. 205-210, or graded viscosities at both the leading and trailing edges of the mobility control slug as disclosed in U.S. Pat. No. 4,018,281 to Chang. Alternatively, the thickening agent concentration may be relatively constant throughout. Normally, the viscosity of at least a portion of the mobility control slug should be at least as great as that of the reservoir oil and typically it will be within the range of about 1 to 4 times the viscosity of the reservoir oil.

Secondary oil recovery may be carried out utilizing injection and production systems as defined by any suitable arrangement of wells. One well arrangement commonly used in waterflooding operations and suitable for use in carrying out the present invention is an integrated five-spot pattern of the type illustrated in U.S. Pat. No. 3,927,716 to Burdyn et al. Other well arrangements may be used in carrying out aspects of the present invention, examples of which are set forth in the Burdyn et al patent. By the term "pore volume" as used herein is meant that volume of the portion of the formation underlying the well pattern employed, as described in greater detail in the Burdyn et al patent.

The mobility control slug may be injected in amounts ranging, e.g., from about 0.1 to about 1.0 pore volumes, more particularly, from about 0.25 to about 0.5 pore volumes.

EXAMPLE 1

Preparation of $(CH_2=CH-CH_2)_2NCH_2CH_2CH_2Br$

A mixture of 200 g diallylamine (Aldrich) and 100 g 3-bromo-1-propanol was refluxed 1 h, cooled, diluted with 400 ml Et$_2$O, washed 1×150 ml saturated K$_2$CO$_3$ plus enough H$_2$O to dissolve the solid. The ether was dried by filtration through 4A sieves, evaporated, and the residue distilled to give 93.6 g (84%) colorless oil bp 63°–67°/0.3 mm Hg which was refluxed 3 h with 340 ml 48% HBr and the HBr removed at reduced pressure to give 160 g (89%) crude product. Crude product was partitioned between saturated K$_2$CO$_3$ and Et$_2$, the Et$_2$O dried with MgSo$_4$ and 4A sieves, stripped, and the product used directly. A portion purified by preparative LC on a Water's Prep-500 using a Silica column and EtOAc: CH$_2$Cl$_2$=20:80 gave characteristic C-13 NMR peaks assigned as follows:

```
        117.1 ppm    57.0      30.8
        (CH2=CH—CH2)2NCH2CH2CH2Br
           135.8     51.4      31.7
```

EXAMPLE 2

Preparation of Polymeric pyrrolidinium Methane Sulfonate

To a dry solution of 2 g (35.9 meq) 88% hydrolyzed poly (vinyl alcohol) (Aldrich, 125,000 Daltons) in 250 ml DMSO under Nitrogen were added 17 ml 0.66 M NaNP in THF (11.2 meq) followed by 15.7 g (72.2 mmole) of the amine prepared according to Example 1. After standing overnight at room temperature, the mixture was heated at 50° C. 2 h with 20 ml CH$_3$I (321 mmole) then the volatiles removed on a Kugelrohr. The residue was dissolved in 400 ml 1:1 H$_2$O:t-BuOH, stirred vigorously, and a solution of 22.5 g NaHSO$_3$ and 9.08 g Na$_2$SO$_3$ added in a minimum of water while air was passed through the flask at 10 ml/min. After 15 h 10 g NaOH were added, the mixture refluxed for 2 hours, then neutralized with 5% HCl. Most of the t-BuOH was removed on a rotary evaporator and the residue dialyzed (Spectrapor Membrane, Arthur H. Thomas Co.) for two days. Filtration and evaporation gave a brittle, dark yellow solid weighing 3.67 g.

It is noted that the above reaction sequence employs a novel cyclization reaction which will be discussed more fully hereinafter and is also discussed in parent U.S. application Ser. No. 373,553, filed Apr. 30, 1982. It is further noted that the diallylaminobromopropane of Example 1 was synthesized by the method of C. D. Hurd and R. J. Sims, *J.A.C.S.*, 68, 2228 (1946). It might have been simpler (and less expensive) to react an alkoxide of a polyvinylalcohol with epichlorohydrin then directly with diallylamine, but, for the present purposes, concerns about possible cross-linking led to the more certain route of Examples 1 and 2. Evidence for conversion of tetraalkylammonium ion to pyrrolidinium ion was seen in the disappearance of the N-14 NMR resonance at −313 ppm and the appearance of a new peak at −303 ppm. [Note: J. P. Kintzinger and J. M. Lehn, *Helv. Chim. Acta.*, 58, 905 (1975)]. The structure and degree of substitution of this pyrrolidinium ion were determined by C-13 NMR with peak positions and are believed to be as follows:

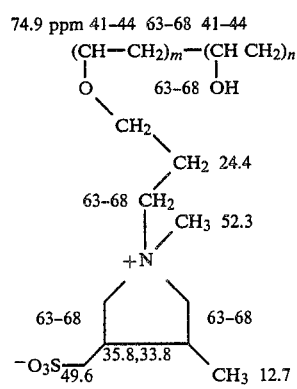

EXAMPLE 3

Viscosity Measurements

The viscosity of 1% solutions of 10 mer % and 20–25 mer % polymeric pyrrolidinium sulfonate derived from 125,000 Dalton poly(vinyl alcohol) in various brines were measured with a Canon size 100 viscometer. Flow times were about 90–220 sec. so that shear rates ranged from 580 to 1400 sec$^{-1}$ [1.27×10$^5$×flow time in sec=Shear rate; Note: J. R. VanWazer et al, "Viscosity and Flow Measurements, a Laboratory Handbook of Rheology", John Wiley, New York 1963].

Such shear rates are felt to be higher than expected for enhanced oil recovery flow and, consequently the viscosities measured are probably quite low compared to what they would be if measured at a lower shear. The results are tabulated in Table 1. The viscosities are promising in view of the low molecular weight and high shear rate.

TABLE 1

Viscosities of 1% Solution of Brine Tolerant Polymers

A - 10% Pyrrolidinium Sulfonate
B - 10-25% Pyrrolidinium Sulfonate

| Salt Concentration | | Viscosity in Centipoise | |
|---|---|---|---|
| | | A | B |
| 0 | NaCl | 1.22 | 2.67 |
| 1 | | — | 1.88 |
| 3 | | — | 1.90 |
| 7 | | 1.21a | 2.10 |
| 10 | | 1.37 | 2.07 |
| 15 | | 1.46 | 2.43 |
| 20 | | 1.63 | 2.62 |
| 30 | | 1.84 | 3.31 |
| 20 | CaBr | 1.60 | 2.06 |

TABLE 1-continued

| Viscosities of 1% Solution of Brine Tolerant Polymers |||
| A - 10% Pyrrolidinium Sulfonate |||
| B - 10-25% Pyrrolidinium Sulfonate |||
|  | Viscosity in Centipoise ||
| Salt Concentration | A | B |
| --- | --- | --- |
| 40 | 2.12 | 3.28 |
| 60 | 2.79 | 3.82 |

[a] at 5% NaCl.

The fairly large drop in viscosity from 0–1% salt is as expected for charged polymers and, as expected, the drop is smaller for the zwitterionic A and smallest for the least derivatized B. The increase in viscosity with further increase in salt was unexpected. Charged polymers either undergo a sudden conformational change to a tertiary structure of lowered hydrodynamic radius or a gradual monotonic collapse when salt level is increased. Polymers A and B on the other hand show an, as yet, unexplained increase in viscosity once the salt level has passed 4–8%.

For A and B part of the increase is due to the increase in viscosity of the salt solutions and would disappear if the viscosity were represented as specific viscosity, but most of the increase is real—and desirable.

Although the above absolute viscosities are relatively low, due to the low molecular weight (125,000) of the polymer used in these exploratory experiments, polymers of molecular weight 500,000 and 1.5 million could be expected to give higher viscosities.

With regard to the previously mentioned cyclization reaction, the reaction of olefins with alkali metal bisulfite, in which the bisulfite adds across the double bond, is known. [M. S. Kharasch, E. M. May. F. R. Mayo, J. Org. Chem., 3, 175 (1938)]. The use of cosolvents [Norton et al, U.S. Pat. No. 3,522,297] and initiators [C. F. Norton, N. F. Seppi, and M. J. Reuter, J. Org. Chem., 33, 4158 (1968)] to promote this reaction is also known as is the use of a certain amount of final sulfonate product as solubilizer in those cases where the olefin is not water soluble [Chen et al U.S. Pat. No. 4,267,123].

It has been discovered, quite unexpectedly, that the course of the reaction is different when two double bonds are present in the same molecule in the relationship $X(CH_2CH=CHR)_2$, where X is as defined hereinafter. By way of illustration, it is known that allyl alcohol produces sodium bisulfite, air, and water. [R. F. Fischer, Inc. and Eng. Chem., 56, 41 (1964)]. This reaction is illustrated as follows.

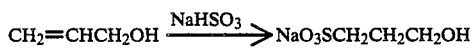

$$CH_2=CHCH_2OH \xrightarrow{NaHSO_3} NaO_3SCH_2CH_2CH_2OH$$

It would be expected that similar treatment of diallyl ether with two or more moles of bisulfite would lead to a disulfonate ether product as follows.

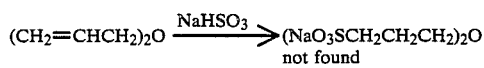

$$(CH_2=CHCH_2)_2O \xrightarrow{NaHSO_3} (NaO_3SCH_2CH_2CH_2)_2O$$
$$\text{not found}$$

Instead, however, there is produced the unexpected tetrahydrofuran derivative as follows.

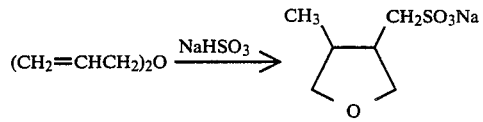

The cyclization reaction of the present invention involves reacting a bisulfite salt and air or oxygen with a polymeric diallylamino compound in an aqueous phase. The reaction proceeds generally at ambient conditions of temperature and pressure, although higher temperatures and pressures may be used if desired. The reaction is carried out in a homogenous aqueous phase. This phase can be water alone, if the olefinic reactant is water soluble. If not, this phase will be a mixture of water and sufficient cosolvent, such as $C_1$–$C_4$ alkanol to dissolve the olefinic reactant.

The bisulfite salt reactant may be any such reactable bisulfite salt such as sodium bisulfite, lithium bisulfite, potassium bisulfite, and ammonium bisulfite. This bisulfite salt may, thus, have the formula $MHSO_3$, where M is Na, Li, K or ammonium.

An oxygen containing gas acts as an initiator. It can be oxygen or air or other molecular oxygen containing gas.

In summary, polymers which can thicken aqueous brine have stability in enhanced oil recovery and in drilling fluids. In oil recovery, brine thickened by water can increase recovery because thickening water raises the viscous force to capillary force ratio which ratio limits the ultimate recovery in secondary waterflooding. In chemical waterflooding a thickened water slug helps maintain the integrity of the surfactant slug. In drilling fluids increased viscosity retards settling of cuttings.

The polymers currently available for these uses are either incapable of tolerating high brines (partially hydrolyzed polyacrylamides) or are not stable hydrolytically (polysaccharides). Consequently, it is desirable to find new polymers which can tolerate both high salt and high temperatures.

New polymers of the present invention can be made from new monomers or by derivatizing known polymers. The latter approach was initially taken with poly (vinyl alcohol) the polymer of choice. Poly (vinyl alcohol) was chosen because it is a cheap polymer, readily available by hydrolysis of polyvinylacetate, and because it has an all carbon backbone which ought to lead to a hydrolytically stable polymer. It was also chosen because partial derivatization would leave water solubilizing hydroxyl groups on the backbone of the polymer.

Poly (vinyl alcohol) has one hydroxyl group for every two carbons, but is not a very water soluble polymer. This is because its compact structure and many hydrogen bonds lead to a high crystal energy [T. H. Kwei in "Macromolecules, An Introduction to Polymer Science", (F. A. Bovey and F. H. Winslow, ed.) Academic Press, New York, 1979, pg. 273]. As little as 10% acetate side chains disrupts the crystal packing and makes the polymer water soluble, but not brine soluble. Incorporation of a modest number of propane sulfonate or pyrrolidinium sulfonate side chains was expected to give far higher water solubility because of the charged nature of those groups.

Charged polymers in water adopt extended conformations to minimize like charge repulsion at the expense of entropy. Higher salt concentrations increase shielding of charges from one another and the polymer contracts to minimize entropy. For example, converting poly (methacrylic acid) to its carboxylate salt by raising the pH gives a much more viscous solution because of chain extension [A. Oth and P. Doty, *J. Phys. Chem.*, 56, 43 (1952)] but raising the NaCl level to as little as 0.5% NaCl results in substantial thinning of solutions of cationic poly (N-butyl-4-vinyl pyridine) [R. M. Fuoss, *Disc. Faraday Soc.*, 11, 125 (1951)]. For simple linear polymers incapable of adopting complex tertiary structures viscosity loss with increasing salt level can be thought of as a loss of the "excess" chain extension of the charged polymer which just returns to the normal entropy determined level of extension of an uncharged polymer.

Particularly in view of this background, it was unexpected that, in contrast to other ionic polymers, viscosity of the polymers of the present invention increased with increasing salinity.

What is claimed is:

1. A method of preparing a polymeric sulfonate comprising a polymeric polyvinyl alcohol backbone having side chain groups of the formula:

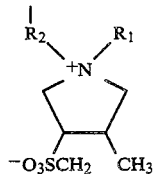
(I)

where:
(i) $R_1$ is $CH_3$, $CH_2CH_3$, $CH_2CH_2OH$, propyl, butyl or phenyl;
(ii) $R_2$ is $(CH_2)_n$ or $$-CH_2-\underset{\underset{OH}{|}}{CH}-CH_2-;$$

and
(iii) n is 1–5, the method comprising reacting a polymeric polyvinyl alcohol backbone having side chain groups of the formula

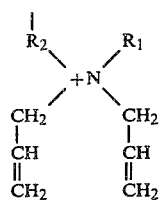

with a bisulfite salt.

2. A method of claim 1 comprising the steps of:
(i) reacting polyvinyl alcohol with $BrCH_2CH_2CH_2N(CH_2CH=CH_2)_2$ in the presence of Na and DMSO in an amount sufficient to convert from about 5% to about 70% of the OH groups of said polyvinyl alcohol into groups of the formula $-CH_2CH_2CH_2N(CH_2CH=CH_2)_2$;
(ii) reacting said $-CH_2CH_2CH_2N(CH_2CH=CH_2)_2$ groups of step (i) with $CH_3I$ to convert said groups into quaternary amino groups of the formula

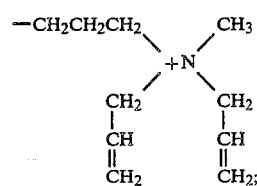

(iii) reacting said quaternary amino groups of step (ii) with $NaHSO_3$ in the presence of oxygen and water to convert said quaternary amino groups into groups of the formula

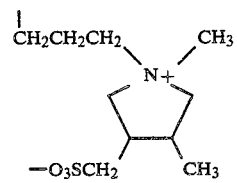

3. A method of claim 2 wherein the sulfonate has a molecular weight of at least 25,000.

4. A method of claim 3 wherein the sulfonate contains from about 5 to 70 mer % of the side chain groups of formula I.

5. A method of claim 4 wherein the sulfonate has a molecular weight of about 30,000 to about 500,000.

6. A method of claim 5 wherein $R_1$ is $CH_3$ or $CH_2CH_3$.

7. A method of claim 6 wherein $R_2$ is $(CH_2)_n$.

8. A method of claim 7 wherein $R_1$ is $CH_3$ and n is 3.

* * * * *